US00PP10613P

United States Patent [19]

Egger et al.

[11] Patent Number: Plant 10,613

[45] Date of Patent: Sep. 22, 1998

[54] ASIATIC HYBRID LILY PLANT 'PAC SUN'

[75] Inventors: Donald L. Egger, Wilsonville; Edward A. McRae, Sandy, both of Oreg.

[73] Assignee: Cebeco Lilies, Inc., Aurora, Oreg.

[21] Appl. No.: 812,489

[22] Filed: Mar. 6, 1997

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Klarquist Sparkman Campbell Leigh & Whinston, LLP

[57] ABSTRACT

A new and distinct Asiatic Lily Hybrid named 'PAC Sun' characterized by having large yellow flowers in a quality inflorescence on genetically dwarf stems with dense foliage excellent for pot plant production.

2 Drawing Sheets

BACKGROUND OF THE INVENTION

The present invention relates to a new and distinct cultivar of Lily hybrid, referred to commercially as an upright Asiatic hybrid pot lily, and given the cultivar name 'PAC Sun'.

This invention was developed by controlled breeding in Aurora, Oreg. using (OH-6 ×OB-4), a proprietary, non-released plant as the seed parent and 9–80, another proprietary, non-released plant as the pollen parent.

This invention has not been observed under all possible environmental conditions. The phenotype may vary significantly with variations in environment such as temperature, light intensity, and day length, without, however, any variation in genotype.

The following traits have been repeatedly observed and are determined to be the basic characteristics of this invention which in combination distinguish this lily as a new and distinct cultivar: 1) large flowers of a bright yellow color with very few spots in a beautiful inflorescence; 2) beautiful, large, yellow green colored buds; 3) genetically dwarf stems excellent for pot plant production; 4) very uniform growth habit; 5) good vigor; and 6) good, dense foliage. Bulbs of this plant may be precooled and forced out of season for uniform pot plant production. In addition, this new lily shows good disease resistance.

This invention is best compared to 'Lemon Pixie' (U.S. Plant No. 6,367). Compared to 'Lemon Pixie', this invention has better flower color, better foliage. Field bulb production of this new plant yields fewer multi-nosed erect concentric bulbs than 'Lemon Pixie'. Multi-nosed bulbs are not salable for commercial forcing. The new plant is also shorter than 'Lemon Pixie' land earlier blooming by one week.

Asexual reproduction of this new variety has been accomplished at Cebeco Lilies, Inc., Aurora, Oreg., by scaling and tissue culture. The resulting plants have shown that the above-mentioned unique features are stable and reproduce true to type in each successive propagation.

Figure 1:
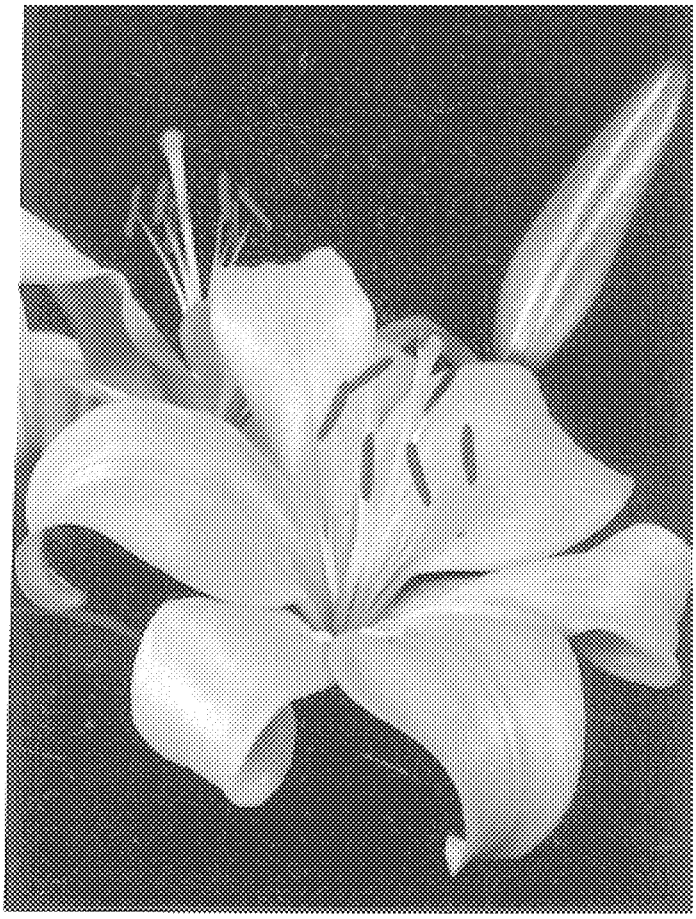
FIG. 1 is a close-up photograph which illustrates in greater detail a single flower of the new plant.
Figure 2:
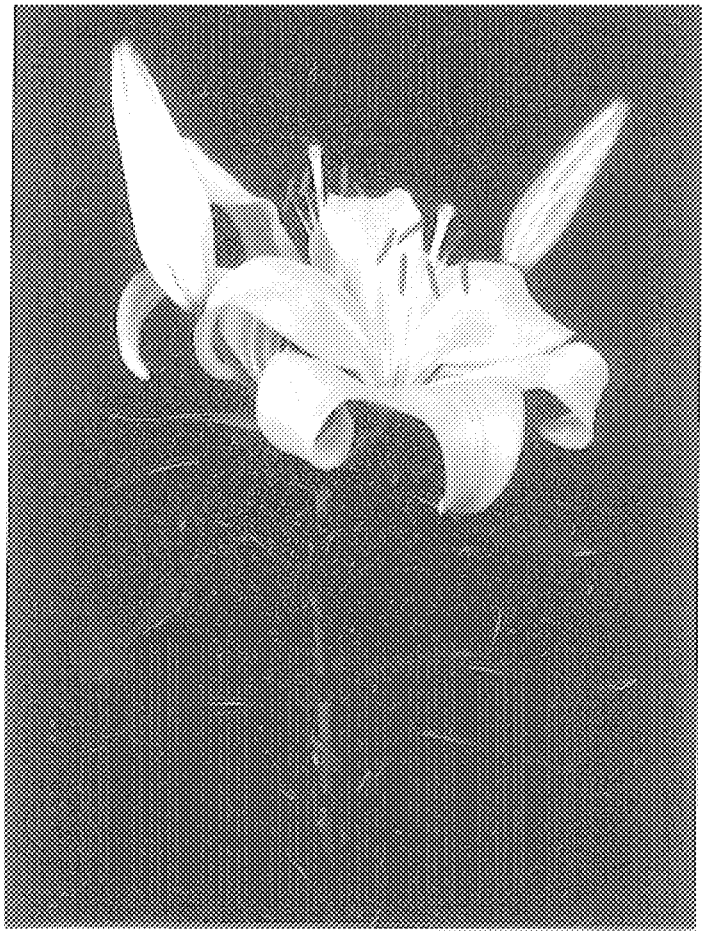
FIG. 2 is a photograph showing the 'PAC Sun' lily.

The photographs of the drawing were taken in June 1996 in a studio and illustrate the typical flower and foliage form, with color as true as reasonably possible in this type of color photograph. This stem was grown in the Cebeco greenhouse in Aurora, Oreg.

DETAILED DESCRIPTION

The following is a detailed description of the invention based on plants produced under commercial practices in the Cebeco Lilies, Inc. fields in Hubbard, Oreg. in July 1996. Color references are made to The Royal Horticultural Society Colour Chart, except where the context indicates a term having its ordinary dictionary meaning.

THE PLANT

Origin: Seedling.

Parentage:

*Seed parent.*—(OH-6 ×OB-5).

*Pollen parent.*—9–80.

Commerical classification: Hybrid Asiatic Lily, pot type.

Classification: Division I-a, according to The Horticultural Classification of Lilies by The Royal Horticultural Society of London.

Form: Single erect stem bearing terminal cluster of flowers.

Height: About 38 cm. from the top of the soil to the top of the flowers from bulbs of 12–14 cm. in circumference.

Stem Color: Yellow green (144A-B) with maroon spots.

Growth habit: Vigorous, upright and rigid.

Internode length: About 1 to 5 mm.

Foliage:

*Arrangement.*—Spiral.

*Leaf size.*—To about 9 cm. long and 0.9 cm wide.

*Leaf shape.*—Lanceolate.

*Texture.*—Leathery.

*Aspect.*—Glossy with long white hairs on leaf margins when young.

*Color.*—Medium green on both sides. Between Yellow Green Group 146A and 147A on the top and 146A on the bottom.

Bulbs:

*Size.*—Variable, ranging to about 12–14 cm. in circumference as used commercially.

*Color.*—White.

THE BUD

Size: Large, to about 7.5 cm. long and 2 cm. wide just prior to opening.

Shape: Ovoid with an obtuse tip.

Rate of Opening: The mature bud opens slowly in response to light.

Color: Yellow green. Yellow Green Group. 144B overlaying Yellow 9A.

THE FLOWER

Blooming habit: Annually, once and early season.

Days to bloom: Flowers approximately 64 days after spring greenhouse planting under typical commercial flower forcing conditions of 15° Celsius night time temperatures.

Flower Size: Medium-large.

*Diameter.*—About 15 cm.

*Depth.*—About 4–5 cm.

Borne: In an umbel-like or modified raceme of 4 flowers from bulbs 12 cm. in circumference.

Shape: When the flower first opens it is a flattened cone shape. Later the shape flattens out more and the tepals reflex slightly at the tips.

Tepalage:

*Number.*—Six.

*Arrangement.*—Imbricated.

*Shape.*—Ovate.

*Texture.*—Spongy.

*Aspect.*—Satiny.

*Size.*—Length: About 9 cm. Width: Inner tepals — about 45 mm. Outer tepals — about 30 mm. Depth of imbrication: About 9 mm.

*Nectary.*—About 2.2 cm. long; with channels together, yellow with white glandular hairs.

*Projections.*—None.

*Spots.*—Very few, up to five spots per flower. Greyed-Purple Group 187A.

*Blush.*—None.

*Color.*—Topside: Intense yellow gold. When the flower opens it is Yellow Group 9A and with maturity darkens to Yellow Group 12A. Bottomside: Intense yellow gold. Yellow Group 12A.

*Discoloration.*—Slightly darker with age as described above.

*Fragrance.*—None.

*Pedicle:*

*Length.*—About 2–4 cm.

*Color.*—Yellow green (144A) overlaid with maroon spots, Greyed-Purple Group 187B.

*Orientation.*—Ascending upwardly in a curve from about 35°–45° from the horizontal.

THE REPRODUCTIVE ORGANS

Stamens:

*Number.*—Six, typical of the genus Lilium.

*Anthers before dehiscence.*—Size: About 19 mm. Color: Light brown. Greyed-Orange Group 163B.

*Filaments.*—Length: About 54 mm. Color: Light yellow. Yellow Group 4D.

*Pollen.*—Color: Orange. Greyed-Orange Group 167A.

Pistil:

*Number.*—One.

*Style.*—Length: About 45–47 mm. Color: Light yellow-green. Yellow Green Group 154C to 154D at base.

Stigma.—Color: Maroon. Red Purple Group 59C.

THE FRUIT

Fertility: Fertile.

Shape: Ovoid.

Color at maturity: Soft brown.

We claim:

1. A new and distinct cultivar of Asiatic hybrid lily plant substantially as herein shown and described.

* * * * *